United States Patent
Choi et al.

(10) Patent No.: US 11,179,443 B2
(45) Date of Patent: Nov. 23, 2021

(54) STABILIZED EXTERNAL PREPARATION COMPRISING THYMOSIN BETA 4 AS AN ACTIVE INGREDIENT

(71) Applicant: G-TREEBNT CO., LTD., Seongnam-si (KR)

(72) Inventors: Jun Won Choi, Seoul (KR); Kyoungsun Kim, Busan (KR); Si Young Lee, Ansan-si (KR); Tae Heum Um, Seoul (KR)

(73) Assignee: G-TREEBNT CO., LTD., Seongnam-si (KR)

( * ) Notice: Subject to any disclaimer, the term of this patent is extended or adjusted under 35 U.S.C. 154(b) by 0 days.

(21) Appl. No.: 15/559,865

(22) PCT Filed: Aug. 4, 2017

(86) PCT No.: PCT/KR2017/008442
§ 371 (c)(1),
(2) Date: Sep. 20, 2017

(87) PCT Pub. No.: WO2018/159906
PCT Pub. Date: Sep. 7, 2018

(65) Prior Publication Data
US 2018/0280479 A1 Oct. 4, 2018

(30) Foreign Application Priority Data
Mar. 3, 2017 (KR) .................. 10-2017-0027706

(51) Int. Cl.
| | | |
|---|---|---|
| *A61K 38/22* | (2006.01) | |
| *A61K 47/38* | (2006.01) | |
| *A61K 47/32* | (2006.01) | |
| *A61K 47/26* | (2006.01) | |
| *A61K 47/10* | (2017.01) | |
| *A61K 47/18* | (2017.01) | |
| *A61K 47/02* | (2006.01) | |
| *A61K 9/00* | (2006.01) | |
| *A61K 9/06* | (2006.01) | |

(52) U.S. Cl.
CPC ........ *A61K 38/2292* (2013.01); *A61K 9/0014* (2013.01); *A61K 9/06* (2013.01); *A61K 47/02* (2013.01); *A61K 47/10* (2013.01); *A61K 47/183* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 6,821,524 B2 * | 11/2004 | Marini | ............ A61K 8/64 424/400 |
| 8,143,218 B2 | 3/2012 | Kleinman et al. | |
| 2009/0047331 A1 | 2/2009 | Kim et al. | |
| 2009/0131313 A1 | 5/2009 | Sosne et al. | |
| 2010/0226911 A1 | 9/2010 | Goldstein | |

FOREIGN PATENT DOCUMENTS

| | | |
|---|---|---|
| CN | 101411871 A | 4/2009 |
| JP | 2009-515873 A | 4/2009 |
| WO | 2008/108927 A2 | 9/2008 |
| WO | 2008/150929 A1 | 12/2008 |

OTHER PUBLICATIONS

Goldstein et al., Expert Opin. Biol. Ther. (2015), 5(Suppl.1): S139-S145. (Year: 2015).*
Sigma-Aldrich, Sodium Carboxymethyl cellulose, accessed on Sep. 20, 2020 at: https://www.sigmaaldrich.com/catalog/substance/sodiumcarboxymethylcellulose12345900432411?lang=en&region=US. (Year: 2020).*

* cited by examiner

*Primary Examiner* — James H Alstrum-Acevedo
*Assistant Examiner* — Tara L Martinez
(74) *Attorney, Agent, or Firm* — Sughrue Mion, PLLC

(57) ABSTRACT

The present invention relates to a stabilized external preparation comprising thymosin beta 4 (Tβ4) as an active ingredient. More specifically, the present invention relates to a therapeutically effective external preparation with improved stability and biological activity of Tβ4. The preparation according to the present invention provides Tβ4 in a stable state by maintaining the biological activity of Tβ4 and minimizing the generation of Tβ4 sulfoxide through oxidization reactions and multimers through aggregation.

6 Claims, 1 Drawing Sheet
Specification includes a Sequence Listing.

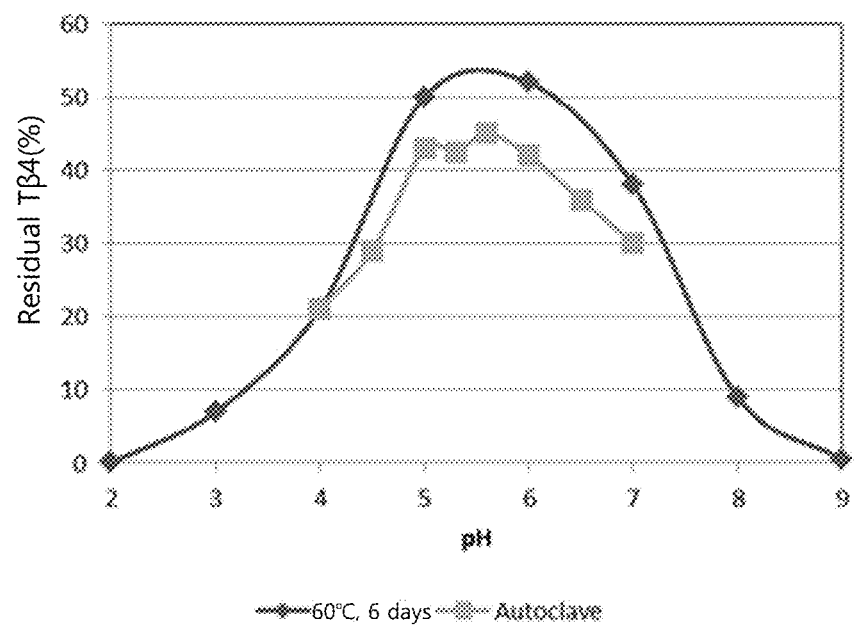

STABILIZED EXTERNAL PREPARATION COMPRISING THYMOSIN BETA 4 AS AN ACTIVE INGREDIENT

CROSS REFERENCE TO RELATED APPLICATIONS

This application is a National Stage of International Application No. PCT/KR2017/008442 filed Aug. 4, 2017, claiming priority based on Korean Patent Application No. 10-2017-0027706 filed Mar. 3, 2017, the contents of all of which are incorporated herein by reference in their entirety.

TECHNICAL FIELD

The present invention relates to a stabilized external preparation comprising thymosin beta 4 (Tβ4) as an active ingredient. More specifically, the present invention relates to a therapeutically effective external preparation with improved stability and biological activity of Tβ4.

BACKGROUND ART

Thymosin beta 4 (Tβ4) represented by SEQ ID NO: 3 is a peptide having forty three (43) amino acids which is acetylated at the N-terminal. It is a naturally-occurring peptide that is found in a variety of tissue and cell types. Tβ4 was originally isolated from a bovine thymus through column chromatography and gel filtration (Low et al., Proc. Nati. Acad. Sci. USA, 78: 1162-1166(1981)). Tβ4 is present in a majority of human tissues and cell types at a molar concentration of $1 \times 10^{-5}$ to $5.6 \times 10^{-1}$, and especially highly occurs in platelets, macrophages and leukocytes.

As identified through Circular Dichroism studies, the Tβ4 molecule has highly dynamic, unstructured and flexible conformations with no secondary structure. However, when its LKKTET (amino acid residues 17-22) interacts with G-actin, such interaction induces the formation of structured N- and C-terminal helices. Also, other parts of the Tβ4 molecule bind to various actin subdomains. Tβ4 binds to G-actin in a 1:1 ratio or an extended conformation. Due to the steric hindrance, the salt-induced actin polymerization is blocked. Tβ4 is a major actin-sequestering molecule in eukaryotic cells. Accordingly, it regulates the assembly and disassembly of the actin filaments that regulate the dynamics of the actin cytoskeleton by maintaining a large pool of actin monomers.

Also, Tβ4 has both wound healing and anti-inflammatory properties. More specifically, Tβ4 is expected to exhibit its therapeutic effects by promoting the migration of keratinocytes and endothelial cells, collagen deposition, and vasculogenesis.

In order for Tβ4 to exhibit sufficient therapeutic effects as a therapeutic agent, its biological activity for a prolonged time but also purity and homogeneity should be maintained. However, as Tβ4 is a polypeptide, chemical and physical changes occur during prolonged storage not only at room temperature but under refrigerated conditions as well. This causes the decrease of its biological activity and therapeutic effects, and the production of its decomposition products, which hinders the preparation of pharmaceutical formulation containing Tβ4.

In relation to this matter, the decomposition pathways of proteins can be divided into two major categories of chemical instability and physical instability. Chemical instability refers to a process that involves deamination reactions forming new decomposition products or the modification of protein structure through the formation or cleavage of peptide bonds. Physical instability refers to denaturation, aggregation and precipitation, etc., that do not involve covalent modifications (Manning et. al., Pharmaceutical Research, 6:903-917(1989); Tallan Stain, Journal of Biological Chemistry. 200: 507-514(1953)). In the chemical decomposition pathway of Tβ4, an impurity in which methionine, among its constituent amino acids, is oxidized to form sulfoxide should be noted. Tβ4 sulfoxide has been reported in the literature (Eur. J. Biochem. 223, 345-350 (1994), Nature Medicine 5(12), 1424 (1999)), and Tβ4 sulfoxide has been reported to exhibit behavior different from that of Tβ4 in actin polymerization or anti-inflammatory action. Therefore, the Tβ4 sulfoxide that is formed during storage of Tβ4 causes changes in pharmacological activity.

DISCLOSURE OF INVENTION

Technical Problem

While carrying out research to provide Tβ4 in a stable state, which can maintain its pharmacological activity at a constant level for prolonged periods, the present inventor completed the present invention by preparing a preparation that contains Tβ4 as an active ingredient and is able to minimize the denaturation thereof.

Accordingly, an object of the present invention is to provide an external preparation with improved stability, comprising Tβ4.

Solution to Problem

To solve the technical problem stated in the above, an aspect of the present invention may provide an external preparation comprising a polypeptide selected from the group consisting of thymosin beta 4 (Tβ4), Tβ4 isoforms having the biological activity of Tβ4, analogues thereof, derivatives thereof, an N-terminal variant of Tβ4 having the biological activity of Tβ4, a C-terminal variant of Tβ4 having the biological activity of Tβ4, LKKTET represented by SEQ ID NO: 1 or a conservative variant thereof, LKKTNT represented by SEQ ID NO: 2 or a conservative variant thereof and combinations thereof; phosphate as a buffer; an additive; and a viscosifier, wherein the additive is selected from the group consisting of disodium-EDTA dihydrate, trehalose, propylene glycol and combinations thereof, and the viscosifier is selected from the group consisting of polyvinyl alcohol, carboxymethyl cellulose, hydroxypropyl methyl cellulose, carbomer and combinations thereof.

Also, according to another aspect of the present invention, an external preparation may be formulated into a form of a gel, a cream, a paste, an ointment, a liniment, a lotion, a hydrogel or an aerosol.

Advantageous Effects of Invention

The preparation according to the present invention, by comprising thymosin (34, phosphate as a buffer, an additive and a viscosifier with certain concentrations, may provide Tβ4 in a stable state by maintaining the biological activity of Tβ4 and minimizing the generation of Tβ4 sulfoxide through oxidation and multimers through aggregation.

DESCRIPTION OF DRAWINGS

FIG. 1 is a graph which shows the stability of Tβ4 of the external preparation according to the present invention depending on the pH.

BEST MODE FOR CARRYING OUT THE INVENTION

The present invention will be described in further detail.

An aspect of the present invention may provide an external preparation comprising a polypeptide selected from the group consisting of thymosin beta 4 (Tβ4), Tβ4 isoforms having the biological activity of Tβ4, analogues thereof, derivatives thereof, an N-terminal variant of Tβ4 having the biological activity of Tβ4, a C-terminal variant of Tβ4 having the biological activity of Tβ4, LKKTET represented by SEQ ID NO: 1 or a conservative variant thereof, LKKTNT represented by SEQ ID NO: 2 or a conservative variant thereof and combinations thereof; phosphate as a buffer; an additive; and a viscosifier, wherein the additive is selected from the group consisting of disodium-EDTA dihydrate, trehalose, propylene glycol and combinations thereof, and the viscosifier is selected from the group consisting of polyvinyl alcohol, carboxymethyl cellulose, hydroxypropyl methyl cellulose, carbomer, and combinations thereof.

Most preferably, the external preparation may comprise an additive selected from the group consisting of disodium-EDTA dihydrate, propylene glycol and combinations thereof, and carboxymethyl cellulose as a viscosifier.

The preparation may comprise distilled water or deionized water as a carrier, and may preferably comprise distilled water.

Most preferably, the polypeptide is thymosin beta 4, and the thymosin beta 4 may be a protein having the amino acid sequence represented by SEQ ID NO: 3.

The term "thymosin beta 4" used herein refers to a protein that is also referred to as Tβ4, which is a 4.9 kDa polypeptide composed of 43 amino acids that was initially isolated from the thymus gland and found in various types of tissue. The protein is up-regulated during in vitro migration and differentiation of endothelial cells, and a variety of thymosin Tβ4 isoforms have been identified.

The term "conservative variant" used herein refers to a variant wherein an amino acid residue has been substituted by a different but biologically similar residue. Examples of substitutions in the conservative variants include substitution of other residues by the hydrophobic residues, e.g., isoleucine, valine, leucine or methionine, and substitution of other residues by polar residues, for example, substitution of lysine by arginine, aspartic acid by glutamic acid, or asparagine by glutamine.

The Tβ4 according to the present invention may have sequence homology of approximately 70%, 75% or 80% or more with known amino acid sequence of Tβ4. The Tβ4 according to the present invention may be applied to an N-terminal variant and a C-terminal variant of wild type Tβ4. More specifically, it may be a polypeptide having the amino acid sequence of SEQ ID NO: 1 or a conservative variant thereof, a polypeptide having the amino acid sequence of SEQ ID NO: 2 or a conservative variant thereof. Tβ4 isoforms include, for example, Tβ4$^{ala}$, Tβ9, Tβ10, Tβ11, Tβ12, Tβ13, Tβ14 and Tβ15. Like Tβ4, the Tβ10 and Tβ15 isoforms, as well as a Tβ4 splice-variant, appear to sequester actin. Tβ4, Tβ10 and Tβ15, as well as other isoforms, share the amino acid sequence LKKTET, which appears to be involved in mediating actin sequestration or binding.

The activity of Tβ4 isoforms is associated with regulation of the actin polymerization mechanism. β-thymosins appear to depolymerize F-actin by sequestering free G-actin. Accordingly, it appears that the ability of Tβ4 to modulate actin polymerization reactions is associated with the activity of binding to actin or sequestering the same through the LKKTET sequence. Accordingly, as with Tβ4, other proteins, including Tβ4 isoforms, which have the amino acid sequence LKKTET and bind to or sequester actin or modulate actin polymerization reactions may, as explained in the present application, be used alone or in combination with Tβ4.

The external preparation may comprise such polypeptides in a concentration of 0.001 to 100 mg/ml, 0.01 to 10 mg/ml, or preferably, 0.1 to 5 mg/ml.

Also, the external preparation may comprise phosphate as a buffer. A buffer may be included to keep the chemical properties of the preparation as consistent as possible despite exposure to external influences or the addition of acids or bases. Especially, by using phosphate as a buffer in the external preparation, the formation of oxidized Tβ4 and other impurities can be minimized. Meanwhile, as a buffering agent, acetate, citrate, histidine, hydrogen carbonate, gluconate, propionate or tromethamine (TRIS) buffers, etc., may be included additionally.

Also, the external preparation may comprise Tβ4 and buffer in a weight ratio of 1:30 to 2:1 or 1:15 to 1:1.

Additives such as disodium-EDTA dihydrate or EDTA, trehalose, and propylene glycol, etc. may be included in order to further improve the storage stability of the external preparation and propylene glycol or a mixture of propylene glycol and disodium-EDTA dihydrate is most preferable.

The external preparation may comprise the additives mentioned above in a concentration of 0.01 to 100 mg/ml, and the concentration may vary depending on the type of an additive substance.

Specifically, disodium-EDTA dihydrate may be contained in a concentration of 0.05 to 2.00 mg/ml, 0.07 to 1.0 mg/ml, or preferably, 0.1 to 0.5 mg/ml. Also, trehalose may be contained in a concentration of 1 to 50 mg/ml, 2 to 30 mg/ml, or preferably, 5 to 20 mg/ml. Also, propylene glycol may be contained in a concentration of 1 to 100 mg/ml, 2 to 50 mg/ml, or preferably, 5 to 20 mg/ml.

Also, the external preparation may comprise, among the additives mentioned in the above, propylene glycol and disodium-EDTA dihydrate in a weight ratio of 500:1 to 1:1, 300:1 to 2:1, 250:1 to 20:1 or 100:1 to 50:1. Also, the external preparation may comprise propylene glycol and trehalose in a weight ratio of 20:1 to 1:20, 10:1 to 1:10 or 3:1 to 1:3. Also, the external preparation may comprise trehalose and disodium-EDTA dihydrate in a weight ratio of 100:1 to 1:1, 50:1 to 2:1, 25:1 to 5:1 or 20:1 to 10:1.

Meanwhile, the viscosifier may be comprised to adjust the viscosity of the external preparation and to minimize the formation of oxidized Tβ4 and other impurities. Examples of the viscosifier may include polyvinyl alcohol, cellulose derivatives such as carboxymethyl cellulose and hydroxypropyl methyl cellulose and carbomer, etc., among which carboxymethyl cellulose is most preferable.

The external preparation may comprise the viscosifiers mentioned above in a concentration of 1 to 100 mg/ml, and the concentration may vary depending on the type of a viscosifier.

Specifically, the polyvinyl alcohol may be contained in a concentration of 1 to 40 mg/ml, 2 to 30 mg/ml, or preferably, 5 to 20 mg/ml. Also, the carboxymethyl cellulose may be contained in a concentration of 1 to 50 mg/ml, 5 to 40 mg/ml, or preferably, 10 to 30 mg/ml. Also, the hydroxypropyl methyl cellulose may be contained in a concentration of 1 to 100 mg/ml, 10 to 100 mg/ml, or preferably, 50 to 100 mg/ml. Also, the carbomer may be contained in a concentration of 2 to 35 mg/ml, 5 to 30 mg/ml, or preferably, 10 to 30 mg/ml.

Also, the additives and viscosifiers may be contained individually or together, and the additives and viscosifiers may be included together in a weight ratio of 1:500 to 1:1, 1:300 to 2:1, or 1:250 to 3:1.

Also, the external preparation preferably contains a mixture of propylene glycol and disodium-EDTA dihydrate as an additive and carboxymethyl cellulose as a viscosifier for the sake of Tβ4 stability. Here, the additive and viscosifier are preferably contained in a weight ratio of 1:300 to 1:2.

Meanwhile, the external preparation may contain a small amount of a preservative agent, which may be, for example, methyl paraben or propyl paraben, alcohols such as chlorobutanol or benzyl alcohol, or guanidine derivatives, and preferably a paraben.

The pH of the external preparation may be in a range of 4 to 7, 4.5 to 6.5, or 5 to 6. To minimize the formation of Tβ4 sulfoxide, the pH is preferably in a range of 5 to 6, or most preferably, 5.5 to 6.0.

Also, the viscosity (cP) of the external preparation may be in a range of 3 to 100,000 at 25° C., and may be adjusted within this range depending on the dosage form while maintaining the stability of the Tβ4.

The formulation of the external preparation may be a gel, a cream, a paste, an ointment, a liniment, a lotion, a hydrogel or an aerosol.

The external preparation according to the present invention may be applicable to a subject in need of treatment of skin wounds such as epidermal injury, etc., for example, mammalian animals, and more specifically, humans, but not limited thereto.

Further, the present invention may provide a method for treating an inflammation or ulcer of the skin, comprising administering the external preparation to the skin of a subject. Specific examples of the inflammation or ulcer may include pressure ulcer, foot ulcer, epidermolysis bullosa, oral mucositis, hidradenitis suppurativa, etc., but not limited thereto.

The present invention may provide a method for treating an inflammation or ulcer of the skin, comprising contacting the external preparation into the skin tissue of a subject. Specifically, the present treatment method may comprise contacting into the skin tissue a gel, a cream, a paste, an ointment, a liniment, a lotion, a hydrogel or an aerosol which comprises the external preparation by a direct application.

The external preparation may be administered concurrently or sequentially in combination with another therapeutic agent, and administered in suitably divided doses several times for a certain period. Specifically, the external preparation may be administered as dose frequency between once a week and twice a day.

The external preparation of the present invention is preferably administered transdermally, and it may be administered via parenteral or intranasal route, or through a mucous membrane, but not limited thereto.

Further, the present invention may provide a method for treating skin damage through wound closure and tissue regeneration, comprising administering the external preparation to the skin of a subject.

Specific administration methods and routes of the treatment method of skin damage are same as described above in the treatment method of an inflammation or ulcer of the skin.

Further, the present invention may provide a use of the external preparation comprising thymosin beta 4 as an active ingredient for use in the prevention or treatment of skin inflammation and ulcer.

Further, the present invention may provide a use of the external preparation comprising thymosin beta 4 as an active ingredient for use in the prevention or treatment of skin damage.

MODE FOR THE INVENTION

Hereinafter, preferred embodiments are provided for further illustration. The following examples are, however, given for the purpose of illustration only, and are not intended to limit the scope of the present invention.

Experimental Example 1: Confirmation of Tβ4 Stability Depending on pH

The experiments for the confirmation of stability depending on pH were carried out over 6 days at 60° C. For pH values 2, 3, 6, 7, and 8, phosphate was used as a 50 mM buffer. For pH 4 and 5, acetate was used, while sodium bicarbonate was used for pH 9. Samples were prepared so that approximately 0.2 mg/mL of Tβ4 could be included in each buffer, and some were autoclaved. Residual Tβ4 was measured in each sample, and the results are shown in FIG. 1. As shown in FIG. 1, it can be found that the pH range where Tβ4 stability is best is from pH 5 to 6.

Experimental Example 2: Comparison of Tβ4 Stability Depending on the Kind of Buffer Tβ4 was dissolved in each of the 30 mM buffers indicated in Table 1 below in a concentration of 1 mg/ml, then stored for 1 week at 40° C. Then reverse phase HPLC was employed to measure changes in Tβ4 content and the total amount of the peaks for impurities. Tβ4 content was measured by comparing the peak areas of the initial sample and the sample stored at 40° C. for 7 days with the peak area of the standard, and the rate of reduction was shown as a percentage (%) of (initial content−content after 1 week)÷ initial content.

Tβ4 oxides (methionine oxidized compound) were measured by comparing the peak area of the methionine oxides based on all peak areas shown during the HPLC analysis as a percentage (%). The rate of increase was shown as the ratio of (area for oxides after 1 week in %−initial area for oxides in %)÷ initial area for oxides in %.

Total impurities were measured by comparing the area of the peaks excluding that for Tβ4 based on all peak areas shown during the HPLC analysis as a percentage (%). The rate of increase was shown as the ratio of (area for total impurities after 1 week in %−initial area for total impurities in %)÷ initial area for total impurities in %.

TABLE 1

| | | | Content (mg/mL) | | | Oxides (Methionine oxidation) | | | Total impurities | | |
|---|---|---|---|---|---|---|---|---|---|---|---|
| No. | Buffer Type* | pH | Initial value | 1 week, 40° C. | Rate of reduction | Initial value | 1 week, 40° C. | Rate of increase | Initial value | 1 week, 40° C. | Rate of increase |
| 1 | Phosphate | 5.0 | 0.96 | 0.90 | 6.2% | 0.38% | 0.51% | 0.34 | 0.40% | 4.12% | 9.30 |
| 2 | Phosphate | 5.5 | 0.97 | 0.92 | 5.2% | 0.46% | 0.59% | 0.28 | 0.44% | 3.70% | 7.41 |
| 3 | Phosphate | 6.0 | 0.99 | 0.93 | 6.1% | 0.60% | 0.70% | 0.17 | 0.37% | 3.60% | 8.73 |
| 4 | Histidine | 5.0 | 0.98 | 0.53 | 45.9% | 0.50% | 2.57% | 4.13 | 0.42% | 29.20% | 68.52 |
| 5 | Histidine | 5.5 | 1.00 | 0.44 | 56.0% | 0.31% | 0.82% | 1.65 | 0.32% | 49.10% | 152.44 |
| 6 | Histidine | 6.0 | 0.99 | 0.92 | 7.1% | 0.29% | 0.90% | 2.10 | 0.32% | 6.42% | 19.06 |
| 7 | Citrate | 5.0 | 0.99 | 0.92 | 7.1% | 0.26% | 1.10% | 3.23 | 0.30% | 5.56% | 17.53 |
| 8 | Citrate | 5.5 | 0.99 | 0.91 | 8.1% | 0.32% | 1.07% | 2.34 | 0.40% | 4.05% | 9.13 |

*The sources of the reagents used in the respective experiments are as follows.
Sodium phosphate dibasic dihydrate: Sigma-Aldrich, Cat#: 71662
Sodium phosphate monobasic monohydrate: Sigma, Cat#: S3522
Histidine: VWR, Cat#: JT2080-5
Citric acid monohydrate: Sigma-Aldrich, Cat#: C1909
Trisodium citrate dihydrate: Sigma-Aldrich, Cat#: S4641

As shown in Table 1, Tβ4 oxides tended to increase more at lower pH (acid). It was confirmed that phosphate as a buffer could maintain the stability of Tβ4.

Experimental Example 3: Comparison of Tβ4 Stability Depending on the Kind of Additive Tβ4 was dissolved in 10 mM phosphate buffer at pH 5.5 in a concentration of 1 mg/ml, and then additives with the contents indicated in Table 2 were dissolved therein. Impurities of the initial state (day 0) in each solution were measured using reverse phase HPLC, and the impurities of each solution stored for 1 week at 40° C. were then measured using reverse phase HPLC.

The additives were employed with the lowest possible concentration in the range of concentrations generally used for external preparations to investigate the influence on Tβ4 at the lowest additive concentration.

Total impurities were measured by comparing the area of the peaks excluding that for Tβ4 based on all peak areas shown during the HPLC analysis as a percentage (%). The rate of increase was shown as the ratio of (area for total impurities after 1 week in %−initial area for total impurities in %)÷ initial area for total impurities in %.

TABLE 2

| | | | Oxides (Methionine oxidation) | | | Total impurities | | |
|---|---|---|---|---|---|---|---|---|
| No. | Additives* | Concentration (mg/ml) | Initial value | 1 week, 40° C. | Rate of increase | Initial value | 1 week, 40° C. | Rate of increase |
| 1 | Propylene Glycol | 10 | 0.34 | 0.28 | −0.18 | 0.52 | 2.00 | 2.85 |
| 2 | Trehalose | 10 | 0.35 | 0.59 | 0.69 | 0.53 | 2.31 | 3.36 |
| 3 | EDTA 2Na | 0.5 | 0.14 | 0.57 | 3.07 | 1.06 | 4.19 | 2.95 |
| 4 | EDTA 2Na + Trehalose | 0.5 + 10 | 0.33 | 0.69 | 1.09 | 1.39 | 4.31 | 2.10 |
| 5 | Propylene Glycol + EDTA 2Na | 10 + 0.5 | 0.44 | 0.49 | 0.11 | 1.31 | 4.05 | 2.09 |
| 6 | Propylene Glycol + Trehalose | 10 + 10 | 0.21 | 0.61 | 1.90 | 1.17 | 4.41 | 2.77 |
| 7 | HPβCD | 10 | 0.34 | 0.57 | 0.68 | 0.60 | 4.60 | 6.67 |
| 8 | PEG 40-Stearate | 10 | 0.44 | 2.36 | 4.36 | 0.44 | 3.17 | 6.20 |
| 9 | PEG 400 | 10 | 0.41 | 3.07 | 6.49 | 0.41 | 3.92 | 8.56 |
| 10 | Tween 20 | 0.5 | 0.20 | 0.37 | 0.85 | 1.43 | 11.09 | 6.76 |

*The sources of the reagents used in the respective experiments are as follows.
Propylene Glycol: Aldrich, Cat#: W294004
Trehalose: Sigma-Aldrich, Cat#: T9449
PEG (Polyethyleneglycol) 40-Stearate: TCI, Cat#: P0721
PEG 400: Merck, Cat#: 807485
HPβCD: (2-Hydroxypropyl)-β-cyclodextrin: Aldrich, Cat#: 332607
Tween 20: Croda International Plc. Product Code: SD40271
EDTA 2Na: Disodium ethylenediaminetetraacetate dihydrate: Sigma, Cat#: E6635

As shown in Table 2, the formation of Tβ4 impurities and oxides was low when propylene glycol, trehalose, and EDTA 2Na were added. Combinations of these also exhibited similar stabilization effects. Meanwhile, HPβCD, which is reported to be a peptide stabilizer, did not have effects, and it was confirmed that oxidized Tβ4 increased sharply with PEG-type additives (PEG 40-Stearate, PEG 400), while the total amount of impurities increased significantly with Tween 20.

Experimental Example 4: Comparison of Tβ4 Stability Depending on the Kind of Viscosifier Tβ4 was dissolved in 10 mM phosphate buffer at pH 5.5 in a concentration of 1 mg/ml, and then viscosifiers with the contents indicated in Table 3 were dissolved therein. Impurities of the initial state (day 0) in each solution were measured using reverse phase HPLC, and the impurities of each solution stored for 1 week at 40° C. were then measured using reverse phase HPLC.

Total impurities were measured by comparing the area of the peaks excluding that for Tβ4 based on all peak areas shown during the HPLC analysis as a percentage (%). The rate of increase was shown as the ratio of (area for total impurities after 1 week in %−initial area for total impurities in %)÷ initial area for total impurities in %.

TABLE 3

| | | | Oxides (Methionine oxidation) | | | Total impurities | | |
|---|---|---|---|---|---|---|---|---|
| No. | Viscosifiers* | Concentration (mg/ml) | Initial value | 1 week, 40° C. | Rate of increase | Initial value | 1 week, 40° C. | Rate of increase |
| 1 | PVA | 10 | 0.31 | 1.34 | 3.32 | 0.46 | 2.39 | 4.18 |
| 2 | HPMC | 10 | 0.27 | 0.46 | 0.71 | 0.38 | 2.05 | 4.39 |
| 3 | CMC | 10 | 0.31 | 0.47 | 0.52 | 0.48 | 2.27 | 3.73 |
| 4 | Carbomer Homopolymer Type B | 10 | 0.41 | 0.75 | 0.83 | 0.35 | 2.86 | 7.16 |
| 5 | Hyaluronate Na | 5 | 0.35 | 1.13 | 2.23 | 0.74 | 7.12 | 8.62 |
| 6 | Xanthan | 10 | 0.34 | 2.94 | 7.63 | 0.34 | 4.82 | 13.16 |
| 7 | Polyvinylpyrrolidone | 20 | 0.87 | 30.18 | 33.69 | 0.87 | 31.18 | 34.84 |
| 8 | Methyl cellulose (4000 cP) | 10 | 0.24 | 0.63 | 1.61 | 0.24 | 3.33 | 12.86 |
| 9 | Polycarbophil | 10 | 0.31 | 0.82 | 1.65 | 0.58 | 11.31 | 18.50 |
| 10 | Gellan gum | 10 | 0.38 | 1.24 | 2.26 | 0.64 | 5.01 | 6.83 |

*The sources of the reagents used in the respective experiments are as follows.
PVA (Polyvinyl alcohol): Sigma-Aldrich, Cat#: 81365
HPMC (Hydroxypropyl methylcellulose): Shin-Etsu, Product ID: Metolose 90SH-100000SR
CMC (Sodium Carboxymethyl cellulose): Ashland, Cat#: 414483
Carbomer Homopolymer Type B: Mutchler Inc. Product Code: Carbopol Mutchle
Hyaluronate Na: Bloomage Freda Biopharma Co. Ltd., Product code: HA-EP1
Xanthan: CP Kelco U.S. Inc., Material #: 10054521
Polyvinylpyrrolidone: Alfa Aesar, Cat#: A14315
Methyl cellulose: Sigma, Cat#: M0512
Polycarbophil: Mutchler Inc. Product Code: Noveonhler I
Gellan gum: Sigma-Aldrich, Cat#: G1910

As shown in Table 3, Tβ4 tended to be stable when the samples contained additives such as polyvinylalcohol, Carbomer Homopolymer Type B, and cellulose-type additives such as HPMC and CMC. Meanwhile, Tβ4 oxides increased sharply in the samples containing polyvinylpyrrolidone, while the total amount of impurities was significantly increased in the samples containing xanthan and polycarbophil than the cases where other additives were added. As for gellan gum, a precipitate that cannot be found by HPLC analysis was formed.

Preparation Examples 1 to 4: Preparation of an External Preparation

Sodium phosphate dibasic, sodium chloride, sodium carboxymethyl cellulose (or HPMC, carbomer) and distilled water were placed in a stainless steel vessel and stirred until completely dissolved. EDTA 2Na, trehalose or propylene glycol was slowly added thereto and stirred. Then, a 10× diluted hydrochloric acid solution was used to adjust the pH to 5.7. Tβ4 was added to the solution, and the pH was measured to confirm that it was in a range of 5 to 6.0. The air bubbles in the gel prepared by depressurizing the vessel were removed to prepare the external preparation according to the examples having the compositions indicated in Table 4.

TABLE 4

| Substance | Example 1 | Example 2 | Example 3 | Example 4 |
|---|---|---|---|---|
| Thymosin β4 | | 172 mg | | |
| Propylene Glycol | 5.75 g | — | — | 5.75 g |
| Trehalose | — | 5.75 g | — | — |
| EDTA 2Na 2H₂O | — | — | 63 mg | 63 mg |
| Carboxymethylcellulose Na | 14.4 g | — | — | 14.4 g |

TABLE 4-continued

| Substance | Example 1 | Example 2 | Example 3 | Example 4 |
|---|---|---|---|---|
| HPMC K4M | — | — | 43.9 g | — |
| Carbomer Homopolymer Type B | — | 11.0 g | — | — |
| Sodium Phosphate Dibasic | | 805 mg | | |
| Sodium Chloride | | 4.03 g | | |
| Sterile Water for | | Amount required to prepare total | | |

TABLE 4-continued

| Substance | Example 1 | Example 2 | Example 3 | Example 4 |
|---|---|---|---|---|
| Injection | amount of 548 g | | | |
| 1:10 HCl Solution | pH adjusted to 5.7 ± 0.1 | | | |

The Tβ4 content and viscosities of the external preparation according to Examples 1 to 4 were measured and shown in Table 5.

TABLE 5

| Substance | Example 1 | Example 2 | Example 3 | Example 4 |
|---|---|---|---|---|
| Content (%) | 106.2 | 80.3 | 76.3 | 102.1 |
| Total impurities (%) | Not detected | 0.64 | 0.78 | 0.37 |
| pH | 5.71 | 5.78 | 5.84 | 5.74 |
| Viscosity (cP) | 3394 | 3621 | 3745 | 2516 |

Whereas viscosity was at levels suitable for use as an external preparation in all examples, the result of content measurement revealed that the content of the preparations of Examples 2 and 3 was lower than Examples 1 and 4. This may be due to the fact that the Tβ4 was not effectively eluted from the prepared preparation.

Experimental Example 5: Confirmation of Stability of the External Preparation

To confirm the stability of the external preparations of Examples 1 and 4, stability test was carried out over 12 months under the conditions of 2-8 r/ambient relative humidity and 25° C., 60% relative humidity. The results were shown in Tables 6 to 9.

TABLE 6

Stability test for the external preparation of Example 1 (2-8° C./ambient relative humidity)

| Test item | Initial value | 3 M | 6 M | 9 M | 12 M | 18 M | 21 M |
|---|---|---|---|---|---|---|---|
| Content (%) | 106.2 | 94.4 | 93.2 | 91.1 | 95.5 | 95.3 | 94.6 |
| Total impurities (%) | Not detected | 2.98 | 3.33 | 3.24 | 3.90 | 4.16 | 4.46 |
| Viscosity (cP) | 3394 | 3604 | 3945 | 3486 | 4168 | 4194 | 3552 |

TABLE 7

Stability test for the external preparation of Example 1 (25° C./60% relative humidity)

| Test item | Initial value | 1 M | 2 M | 3 M | 6 M | 9 M | 12 M |
|---|---|---|---|---|---|---|---|
| Content (%) | 106.2 | 101.0 | 100.8 | 99.1 | 96.5 | 93.7 | 79.9 |
| Total impurities (%) | Not detected | 2.82 | 3.21 | 3.31 | 6.16 | 6.10 | 19.49 |
| Viscosity (cP) | 3394 | 3460 | 3329 | 3525 | 4128 | 3984 | 4272 |

TABLE 8

Stability test for the external preparation of Example 4 (2-8° C./ambient relative humidity)

| Test item | Initial value | 3 M | 6 M | 9 M | 12 M | 18 M | 24 M |
|---|---|---|---|---|---|---|---|
| Content (%) | 102.1 | 101.3 | 102.2 | 105.2 | 103.3 | 107.0 | 105.9 |
| Total impurities (%) | 0.37 | 1.66 | 1.30 | 1.14 | 3.24 | 0.92 | 2.95 |
| Viscosity (cP) | 2516 | 2660 | 2818 | 2621 | 2804 | 2857 | 2713 |

TABLE 9

Stability test for the external preparation of Example 4 (25° C., 60% relative humidity)

| Test item | Initial value | 1 M | 2 M | 3 M | 6 M | 9 M | 12 M |
|---|---|---|---|---|---|---|---|
| Content (%) | 102.1 | 101.4 | 103.1 | 101.0 | 102.8 | 105.9 | 105.9 |
| Total impurities (%) | 0.37 | 1.38 | 2.70 | 3.15 | 2.52 | 3.46 | 5.37 |
| Viscosity (cP) | 2516 | 2778 | 2739 | 2634 | 2883 | 3054 | 2795 |

As shown in Tables 6 and 7, the external preparations of Examples 1 and 4 were found to remain stable enough for medical use for 2 years when stored at 2 to 8° C. Especially, the preparation of Example 4 was found to have superior stability even under the relatively harsh condition of 25° C., 60% relative humidity.

An embodiment of the present invention has been described in the above, but a person having ordinary skill in the art will be able to apply various modifications and changes to the present invention without departing from the spirit of the present invention as indicated in the attached claims by including, modifying, deleting or adding components, and such shall be said to be included within the scope of the present invention.

What is claimed is:

1. A method for treating skin damage of a subject, comprising administering an external preparation to a damaged site of a skin of the subject,
   wherein the treatment of the skin damage includes wound closure and tissue regeneration;
   wherein the external preparation comprises
      thymosin beta 4 (Tβ4) as an active ingredient in an amount of 172 mg based on the total amount 548 g of the external preparation,
      a phosphate buffer;
      an additive that is propylene glycol in an amount of 5.75 g and/or disodium-EDTA dihydrate in an amount of 63 mg, both based on the total amount 548 g of the external preparation; and
      a sodium carboxymethyl cellulose as a viscosifier, in an amount of 14.4 g based on the total amount 548 g of the external preparation; and
   wherein the external preparation has a pH of 5.5-6.0.

2. The method of claim 1, wherein the skin damage is pressure ulcer, foot ulcer, epidermolysis bullosa, oral mucositis, or hidradenitis suppurativa.

3. The method of claim 2, wherein the skin damage comprises inflammation.

4. The method of claim 1, wherein the viscosity (cP) of the external preparation is in a range of 3 to 100,000 at 25° C.

5. The method of claim 1, wherein the external preparation is formulated into a form of a gel, a cream, a paste, an ointment, a liniment, a lotion, a hydrogel or an aerosol.

6. A method for treating skin damage of a subject, comprising administering an external preparation to a damaged site of a skin of the subject,
   wherein the treatment of the skin damage includes wound closure and tissue regeneration;
   wherein the external preparation comprises
      thymosin beta 4 (Tβ4) as an active ingredient in an amount of 172 mg based on the total amount 548 g of the external preparation,
      a phosphate buffer,
      an additive that is propylene glycol in an amount of 5.75 g and/or disodium-EDTA dihydrate in an amount of 63 mg, both based on the total amount 548 g of the external preparation; and
      a sodium carboxymethyl cellulose as a viscosifier, in an amount of 14.4 g based on the total amount 548 g of the external preparation,
      sterile water,
      sodium chloride, and
      HCl to adjust a pH of the external preparation to 5.5-6.0.

* * * * *

```
                        SEQUENCE LISTING

<160> NUMBER OF SEQ ID NOS: 3

<210> SEQ ID NO 1
<211> LENGTH: 6
<212> TYPE: PRT
<213> ORGANISM: Homo sapiens

<400> SEQUENCE: 1

Leu Lys Lys Thr Glu Thr
1               5

<210> SEQ ID NO 2
<211> LENGTH: 6
<212> TYPE: PRT
<213> ORGANISM: Homo sapiens

<400> SEQUENCE: 2

Leu Lys Lys Thr Asn Thr
1               5

<210> SEQ ID NO 3
<211> LENGTH: 43
<212> TYPE: PRT
<213> ORGANISM: Artificial Sequence
<220> FEATURE:
<223> OTHER INFORMATION: Synthetic construct (thymosine beta 4)

<400> SEQUENCE: 3

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40
```